(12) United States Patent
Ralph

(10) Patent No.: US 12,064,098 B2
(45) Date of Patent: *Aug. 20, 2024

(54) NEEDLE DEVICE WITH ACTIVATION FORCE LIMITER

(71) Applicant: Gyrus ACMI, Inc, Southborough, MA (US)

(72) Inventor: Christopher R. Ralph, Woodinville, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 475 days.

This patent is subject to a terminal disclaimer.

(21) Appl. No.: 17/199,725

(22) Filed: Mar. 12, 2021

(65) Prior Publication Data

US 2021/0196252 A1    Jul. 1, 2021

Related U.S. Application Data

(63) Continuation of application No. 15/995,593, filed on Jun. 1, 2018, now Pat. No. 10,945,714.

(51) Int. Cl.
*A61B 10/02* (2006.01)
*A61B 90/00* (2016.01)

(52) U.S. Cl.
CPC ...... *A61B 10/0283* (2013.01); *A61B 10/0266* (2013.01); *A61B 90/03* (2016.02); *A61B 2010/0208* (2013.01); *A61B 2090/034* (2016.02)

(58) Field of Classification Search
CPC . A61B 10/0283; A61B 90/03; A61B 10/0266; A61B 2090/034; A61B 2010/0208

USPC ......................................................... 600/565
See application file for complete search history.

(56) References Cited

U.S. PATENT DOCUMENTS

| | | |
|---|---|---|
| 10,945,714 B2 | 3/2021 | Ralph |
| 2010/0069786 A1 | 3/2010 | Globerman et al. |
| 2017/0105763 A1 | 4/2017 | Karve et al. |
| 2019/0365362 A1 | 12/2019 | Ralph |

OTHER PUBLICATIONS

"U.S. Appl. No. 15/995,593, Examiner Interview Summary mailed Nov. 10, 2020", 3 pgs.
"U.S. Appl. No. 15/995,593, Final Office Action mailed Aug. 13, 2020", 7 pgs.
"U.S. Appl. No. 15/995,593, Non Final Office Action mailed Mar. 31, 2020", 14 pgs.
"U.S. Appl. No. 15/995,593, Notice of Allowance mailed Nov. 20, 2020", 8 pgs.
"U.S. Appl. No. 15/995,593, Response filed Jun. 12, 2020 to Non Final Office Action mailed Mar. 31, 2020", 6 pgs.
"U.S. Appl. No. 15/995,593, Response filed Nov. 5, 2020 to Final Office Action mailed Aug. 13, 2020", 6 pgs.

*Primary Examiner* — Puya Agahi
*Assistant Examiner* — Chanel J Jhin
(74) *Attorney, Agent, or Firm* — Schwegman Lundberg & Woessner, P.A.

(57) ABSTRACT

A medical instrument having an aspiration needle, handle device and an actuation force limiter. The actuation force limiter provides an active or passive force release mechanism that keeps the force from overpowering operation of the needle.

9 Claims, 6 Drawing Sheets

NEEDLE DEVICE WITH ACTIVATION FORCE LIMITER

PRIORITY CLAIM

This application is a continuation application of U.S. patent application Ser. No. 15/995,593, filed on Jun. 1, 2018, the contents of which are hereby incorporated by reference.

BACKGROUND

The statements in this section merely provide background information related to the present disclosure and may not constitute prior art.

Needle aspiration devices, such as transbronchial needle aspiration (TBNA) devices, are used to collect samples from target tissue, such as tumors and nodules, for analysis. Activation of a needle requires a distal force applied by an operator interacting with a handle of the device. The distal end of the needle may deflect or buckle if the applied activation force exceeds the translational strength of the needle, thus reducing its effectiveness.

SUMMARY

The present invention provides an example medical instrument for sampling tissue. The example medical instrument includes a handle that controls the force required for a user to activate the needle and provides an active or passive force limiting device.

An exemplary medical device includes a needle having a distal end and a proximal end, the distal end includes a piercing tip and the proximal end comprises a shaft section having a groove, and a handle including a handle body having a lumen, and a needle actuator including a handle portion, and a shaft portion slidably received within the handle body, the shaft portion comprising: a flexible engagement member having a first end attached to the shaft portion and a second end opposite the first end, the second end having a protrusion, wherein the flexible engagement member is configured to be flexible thus allowing the protrusion to move in a direction perpendicular to a longitudinal axis of the handle, wherein the protrusion maintains engagement with the groove while a distal force applied to the actuator section remains below a predefined threshold value, when the distal force is greater than the predefined threshold value, the protrusion disengages from the groove by overcoming a frictional force between the protrusion and the groove.

A method of using a medical device includes providing a needle having a distal end and a proximal end, the distal end comprises a piercing tip and the proximal end comprises a shaft section having a groove, providing a handle comprising: a handle body having a lumen, and a needle actuator including a handle portion, and a shaft portion slidably received within the handle body, the shaft portion comprising a flexible engagement member having a first end attached to the shaft portion and a second end opposite the first end, the second end having a protrusion, wherein the flexible engagement member is configured to be flexible thus allowing the protrusion to move in a direction perpendicular to a longitudinal axis of the handle, transmitting a first distal force applied to the handle portion of the needle actuator to the shaft section and the piercing tip of the needle, wherein the first distal force is below a predefined threshold value, and disengaging the flexible engagement member from the groove in response to the needle actuator receiving a second distal force being greater than the predefined threshold value.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 illustrates an side view of the aspiration device of FIG. 1-1 in an activated state in accordance with principles of the present invention;

FIG. 2 illustrates a cross-sectional view of the aspiration device of FIG. 1-1;

FIG. 6-1 illustrates an exemplary passive release mechanism;

FIG. 6-2 illustrates an exemplary passive release mechanism;

FIG. 6-3 illustrates an exemplary passive release mechanism; and

DETAILED DESCRIPTION

The following description is merely exemplary in nature and is not intended to limit the present disclosure, application, or uses.

Figure 1:
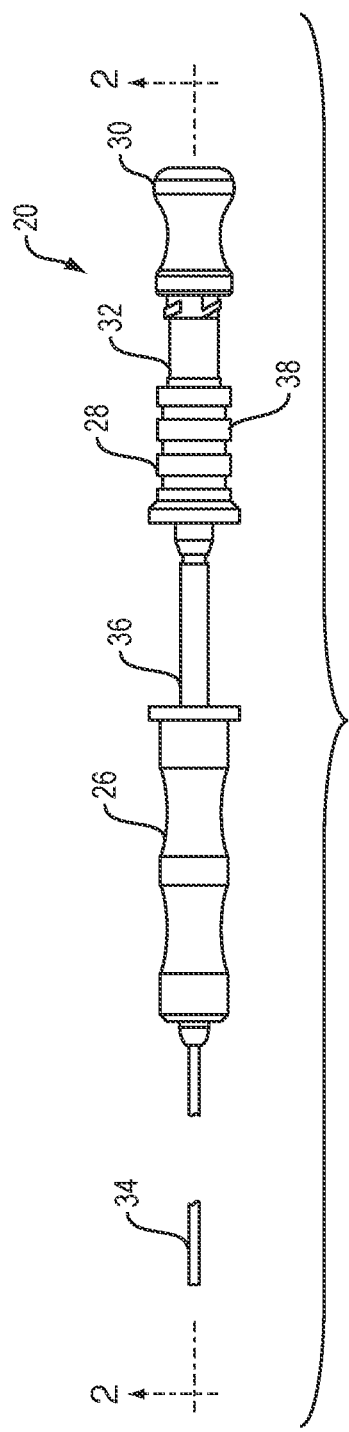
FIG. 1-1 illustrates an side view of an aspiration device in a deactivated state in accordance with principles of the present invention.
Figures 1, 2:
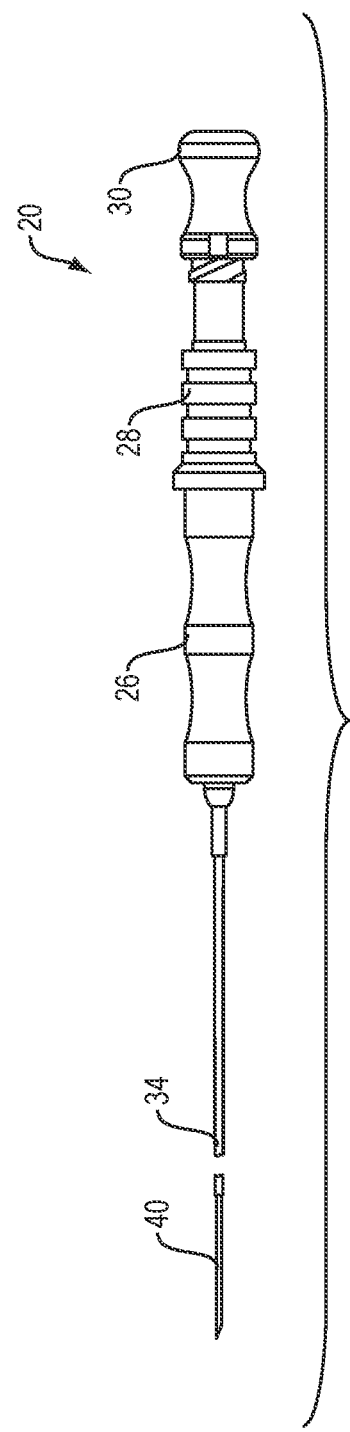
Figure 2:
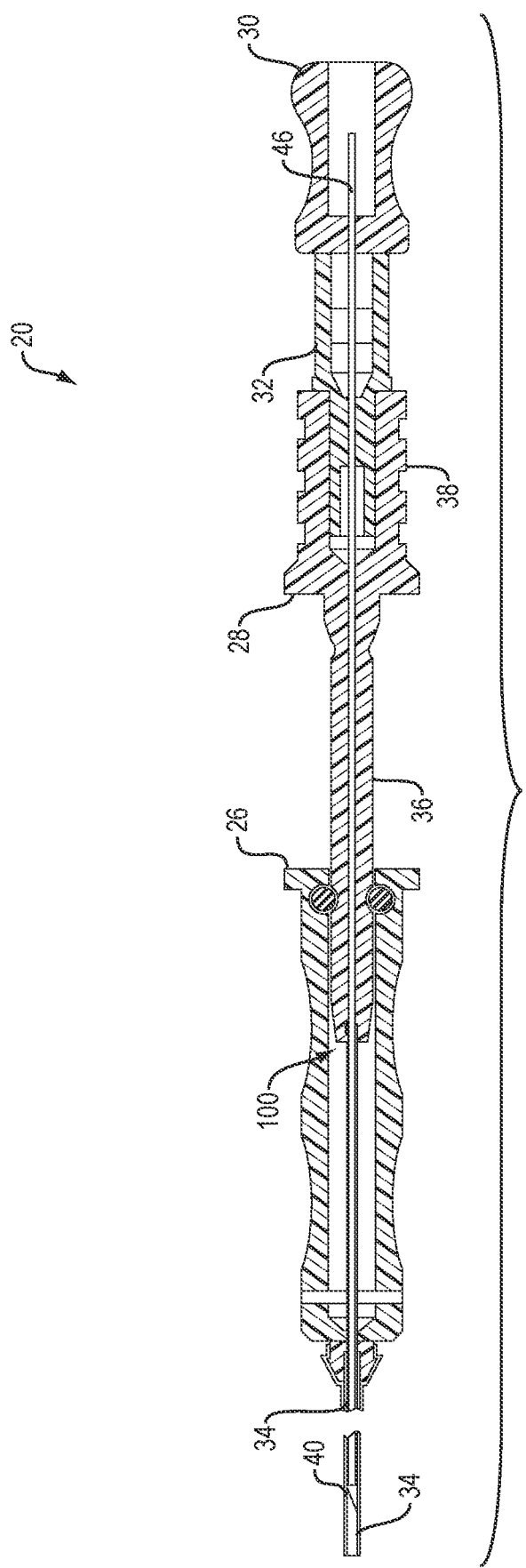

FIGS. 1-1 and 2 illustrate an example needle aspiration device 20 (e.g., transbronchial needle aspiration (TBNA) device) in a deactivated position and FIG. 1-2 illustrates the device 20 in an activated position. The device 20 includes a handle having a handle body 26, a needle actuator 28, a stylet knob 30 and a Luer component 32. The handle body 26 is attached to a proximal end of a sheath 34. The needle actuator 28 includes a shaft portion 36 coupled to a handle portion 38. The needle actuator 28 receives and makes contact with a proximal end of a needle 40 that is slidably received within the sheath 30. An active release mechanism 100 is incorporated into the interface between the needle actuator 28 and the needle 40 and/or a passive release mechanism (not shown) is incorporated into a portion of a shaft of the needle 40 proximal from a distal tip of the needle 40. The stylet knob 30 is attached to a proximal end of a stylet 46 that is slidably received within the needle 40. A distal end of a Luer component 32 is attached to a cavity of the handle portion 38 of the needle actuator 28.

In the deactivated position, the distal end of the needle 40 is retracted within the sheath 34 (FIGS. 1-1 and 2). In the activated position, the distal end of the needle 40 is exposed beyond the distal end of the sheath 34 (FIG. 1-2).

The shaft portion 36 is slidably received within a cavity (i.e., lumen) of the handle body 26. At a proximal end of the cavity of the handle body 26 is an annular groove that receives at least a portion of an O-ring. The O-ring keeps the shaft portion 36 from being easily removed from the handle body 26.

Figure 7:
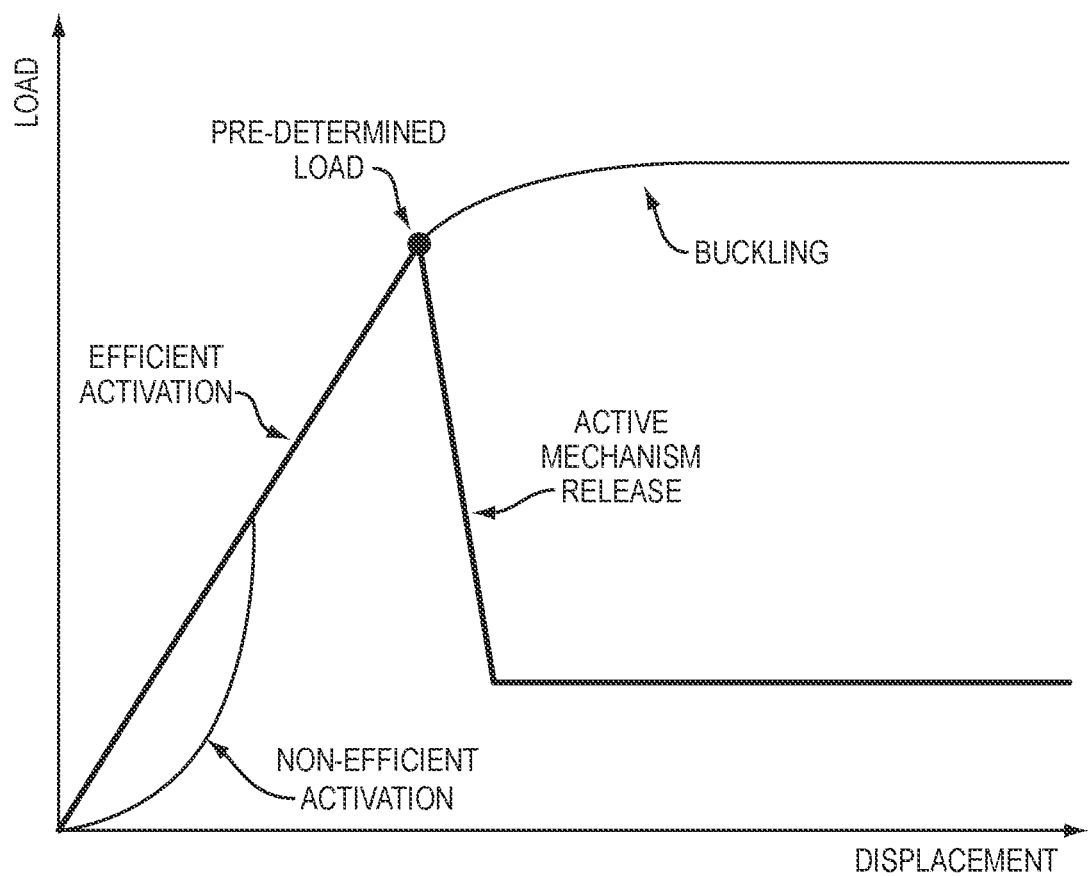
FIG. 7 illustrates a graph of needle loading relative to the active and passive release mechanisms shown in the previous figures.

A user initiates needle activation by applying a distal force to the handle portion 38 of the needle actuator 28 without applying the distal force to the handle body 26. If the distal force exceeds a predefined threshold (e.g., pre-determined load; FIG. 7), the active or passive release mechanisms are activated causing a lease of or a reduction of the applied distal force.

Figure 3:
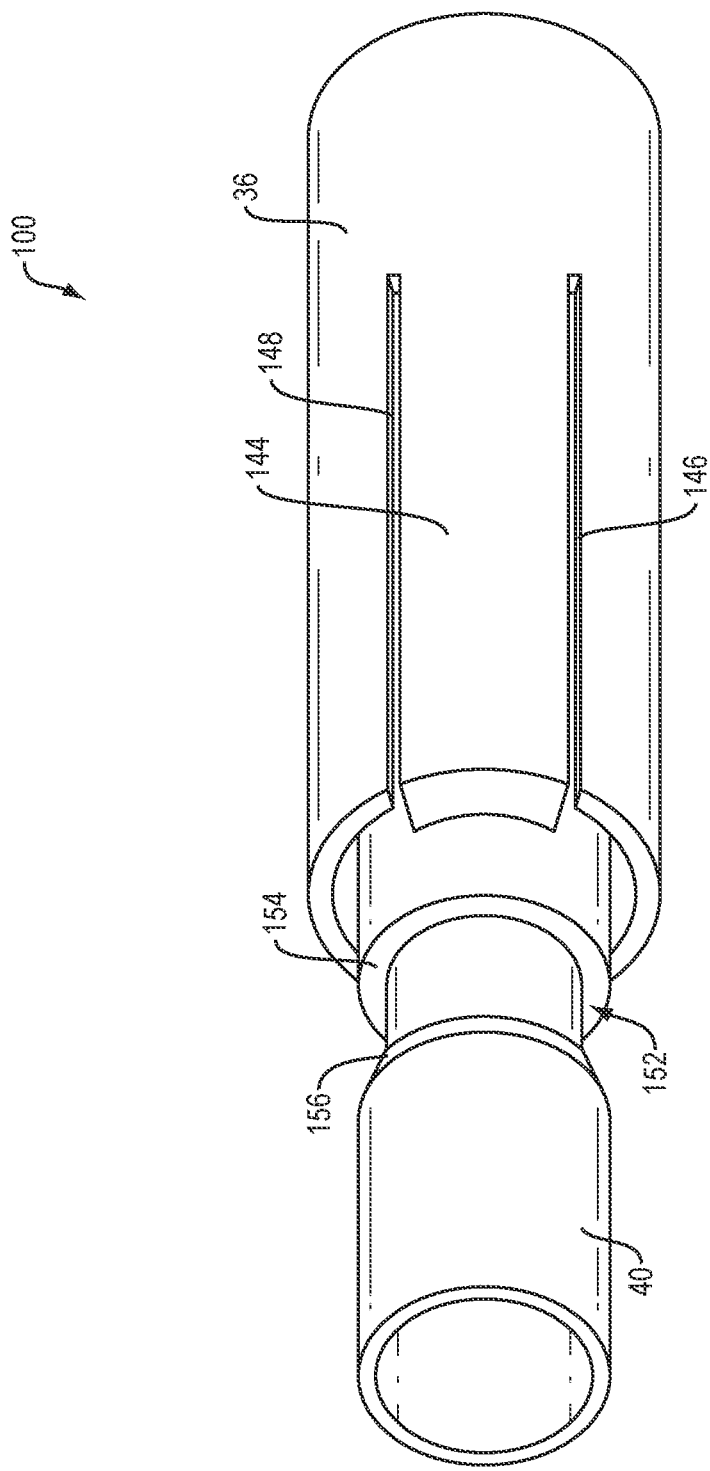
FIG. 3 illustrates a perspective side view of an active release mechanism of the aspiration device of FIG. 2 in a preassembled configuration.
Figure 4:
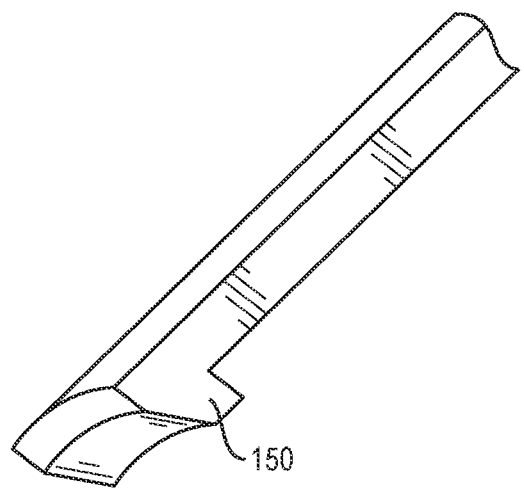
FIG. 4 illustrates a perspective view of a deflecting/flexible portion of the active release mechanism of FIG. 3.
Figure 5:
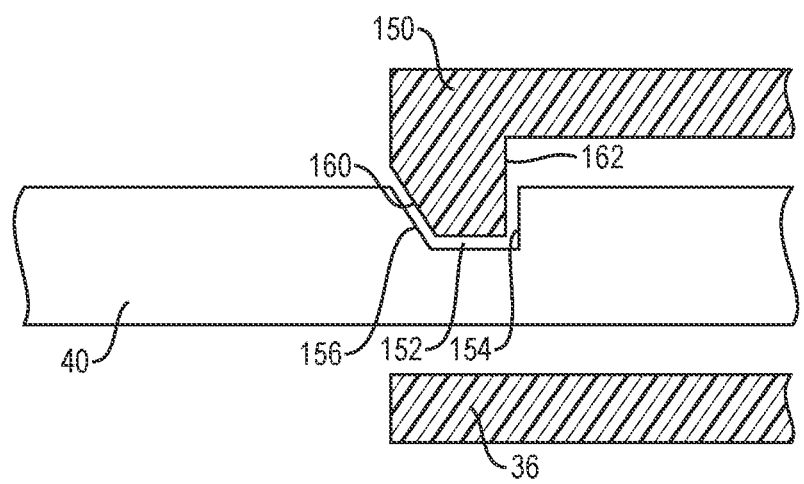
FIG. 5 illustrates a cross-sectional view of a portion of the needle actuator and the needle shaft of FIG. 3.

FIGS. 3, 4 and 5 show various views of at least part of the active release mechanism 100. FIG. 3 shows the active release mechanism 100 before assembly. In one embodiment, the active release mechanism 100 includes a proximal end of the needle 40 that is slidably received within a distal end of the shaft portion 36. The distal end of the shaft portion 36 includes a flexible engagement member 144. The flexible engagement member 144 is attached at its proximal end to a body of the shaft portion 36. Edges of the flexible engagement member 144 are defined by longitudinal slats 146 and 148 that separate the edges of the flexible engagement member 144 from the rest of the shaft portion 36. A distal end of an interior side of the flexible engagement member 144 includes a slot engaging protrusion 150. The slot engaging protrusion 150 includes a leading edge 160 and a trailing edge 162. The leading edge 160 includes a normal vector that is not parallel to a longitudinal axis of the needle 40. The trailing edge 162 includes a normal vector that is approximately parallel to the longitudinal axis of the needle 40.

A proximal end of the needle 40 includes an annular groove 152 configured to receive the slot engaging protrusion 150 of the flexible engagement member 144. The annular groove 152 includes a leading edge 156 configured to engage with the leading edge 160 of the slot engaging protrusion 150. The annular groove 152 also includes a trailing edge 154 configured to engage with the trailing edge 162 of the slot engaging protrusion 150. In one embodiment, the normal vectors of the trailing edges 154, 162 are parallel to a longitudinal axis of the needle 40. The normal vectors for the trailing edges 154, 162 may not be parallel to the longitudinal axis of the needle 40, as long as when the trailing edges 154, 162 make contact with each other, they allow a proximal force applied to the needle actuator 28 to move the needle proximally.

In one embodiment, the normal vectors of the leading edges 156, 160 are not parallel to the longitudinal axis of the needle 40. The angular value for the difference between the normal vectors of the leading edges 156, 160 and the longitudinal axis of the needle 40 is chosen to allow the slot engaging protrusion 150 slide out of the annular groove 152, when a predefined distal force (i.e., the threshold value (e.g., pre-determined load; FIG. 7)) has been applied to the needle actuator 28.

In one embodiment, surfaces of the leading edges 156, 160 are chosen to exhibit a predefined amount surface friction between the leading edges 156, 160. The distal force needed to overcome the surface friction is equivalent to the threshold value (e.g., pre-determined load; FIG. 7).

In operation, a user engages the handle portion 38 and applies a force in the distal direction in order to drive the needle 40 out of the sheath 34 and into target tissue for aspirating a tissue sample. The angular value for the leading edges 156, 160 and/or flexibility in the radial direction of the flexible engagement member 144 are selected such that when the distal force becomes greater than a predefined actuation force maximum, the slot engaging protrusion 150 will disengage from the annular groove 152. Disengagement of the slot engaging protrusion 150 from the annular groove 152 disengages or reduces the distal force applied to the handle portion 38 from translating to the needle 40.

After disengagement of the slot engaging protrusion 150 from the annular groove 152, re-engagement can occur simply by retracting the shaft portion 36 until the slot engaging protrusion 150 re-engages with the annular groove 152 with the trailing edges 154, 162 making contact.

Figures 1, 6:
Figures 2, 6:
Figures 3, 6:
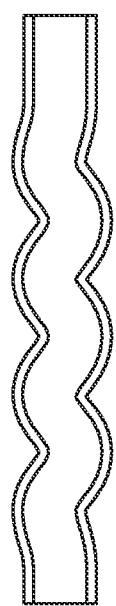

FIGS. 6-1, 6-2 and 6-3 show cross-sectional views of various needle shafts displaying the passive release mechanism. These passive release mechanisms are implemented as various buckling modes of the shaft of the needle 40 proximal from a tip of the needle 40. In one embodiment, the shaft of the needle 40 is implemented with a buckling feature within the handle body 26 of the needle aspiration device 20 and the proximal end of the shaft of the needle 40 is affixed to the needle actuator 28. FIG. 6-1 shows the needle shaft exhibiting Euler buckling. FIG. 6-2 shows the needle shaft exhibiting sheer crimping. FIG. 6-3 shows the needle shaft exhibiting face sheet wrinkling. These buckling features of the shaft are configured to be activated once the distal activation force exceeds a predefined maximum threshold value (e.g., pre-determined load; FIG. 7). Once one of the buckling occurs, a distal force is still applied to the distal end of the needle, however the force is below a previously determined needle tip failure value.

In one embodiment, once the distal activation force drops below the predefined maximum threshold value, the needle shafts may return to their pre-non-buckled state. This allows for repeat needle activation.

FIG. 7 illustrates a load versus displacement graph of activation force is applied to the needle systems described above. The predetermined load value is a value less than a value that would cause failure of the needle tip.

EMBODIMENTS

A. A medical device comprising: a needle having a distal end and a proximal end, the distal end comprises a piercing tip and the proximal end comprises a shaft section having a groove; and a handle comprising: a handle body having a lumen; and a needle actuator comprising: a handle portion; and a shaft portion slidably received within the handle body, the shaft portion comprising: a flexible engagement member having a first end attached to the shaft portion and a second end opposite the first end, the second end having a protrusion, wherein the flexible engagement member is configured to be flexible thus allowing the protrusion to move in a direction perpendicular to a longitudinal axis of the handle; wherein the protrusion maintains engagement with the groove while a distal force applied to the actuator section remains below a predefined threshold value, when the distal force is greater than the predefined threshold value, the protrusion disengages from the groove by overcoming a frictional force between the protrusion and the groove.

B. The medical device of B, wherein the engagement between the protrusion and the groove is configured to transmit any distal force applied to the needle actuator to the piercing tip of the needle, the transmitted distal force being at a value less than the predefined threshold value.

C. The medical device of B, wherein the protrusion comprises a radially flexible feature incorporated into the shaft section of the needle actuator.

D. The medical device of A, wherein at least one of materials and surface friction properties between the protrusion and the groove are selected to allow for disengagement when the applied distal force is greater than the predefined threshold value.

E. The medical device of A, wherein the predefined threshold value is based at least on translation strength properties of the tip of the needle.

F. The medical device of A, wherein the protrusion and the groove are configured to reengage after disengagement and after proximal movement of the actuator section relative to the shaft section.

G. A method of using a medical device comprising: providing a needle having a distal end and a proximal end, the distal end comprises a piercing tip and the proximal end comprises a shaft section having a groove; and providing a handle comprising: a handle body having a lumen; and a needle actuator comprising: a handle portion; and a shaft portion slidably received within the handle body, the shaft portion comprising: a flexible engagement member having a first end attached to the shaft portion and a second end opposite the first end, the second end having a protrusion, wherein the flexible engagement member is configured to be flexible thus allowing the protrusion to move in a direction perpendicular to a longitudinal axis of the handle; transmitting a first distal force applied to the handle portion of the needle actuator to the shaft section and the piercing tip of the needle, wherein the first distal force is below a predefined threshold value; and disengaging the flexible engagement member from the groove in response to the needle actuator receiving a second distal force being greater than the predefined threshold value.

H. The method of G, wherein the flexible engagement member comprises a radially flexible feature incorporated into the shaft portion of the needle actuator.

I. The method of G, wherein at least one of materials and surface friction properties between the protrusion and the groove are selected to allow for disengagement when the applied distal force is greater than the predefined threshold value.

J. The method of G, wherein the predefined threshold value is based at least on translation strength properties of the tip of the needle.

K. The method of G, further comprising: after disengaging, receiving a proximal movement of the actuator section relative to the shaft section; and reengaging the protrusion and the groove in response to receiving the proximal movement.

The description of the invention is merely exemplary in nature and variations that do not depart from the gist of the invention are intended to be within the scope of the invention. Such variations are not to be regarded as a departure from the spirit and scope of the invention.

What is claimed is:

1. A method of using a medical device comprising:
   providing a needle having a distal end and a proximal end, the distal end comprising a piercing tip and the proximal end comprising a shaft section having a groove;
   providing a handle comprising:
   a handle body having a lumen; and
   a needle actuator comprising:
   a handle portion; and
   a shaft portion slidably received within the handle body, the shaft portion comprising:
   a flexible engagement member configured to receive the shaft section of the needle, the flexible engagement member having a first end attached to the shaft portion and a second end opposite the first end, the second end having a protrusion configured to engage the groove in the shaft section of the needle, wherein the flexible engagement member is configured to be flexible thus allowing the protrusion to move in a direction perpendicular to a longitudinal axis of the handle;
   transmitting, through interaction between the protrusion and the groove, a first longitudinal force applied in a distal direction to the handle portion of the needle actuator to the shaft section and the piercing tip of the needle, wherein the first longitudinal force is below a predefined threshold value; and
   disengaging the flexible engagement member from the groove in response to application of a second longitudinal force applied in the distal direction to the handle portion, the second longitudinal force being greater than the predefined threshold value.

2. The method of claim 1, wherein the flexible engagement member comprises edges defined by longitudinal slots in the shaft portion of the needle actuator.

3. The method of claim 1, wherein materials or surface friction properties of the protrusion or the groove are selected to allow for disengagement when the applied second longitudinal force is greater than the predefined threshold value.

4. The method of claim 1, wherein the predefined threshold value is based at least in part on translation strength properties of the piercing tip of the needle.

5. The method of claim 1, further comprising:
   after disengaging, receiving a proximal movement of the needle actuator relative to the shaft section; and
   reengaging the protrusion and the groove in response to the proximal movement realigning the groove and the protrusion.

6. The method of claim 1, further comprising moving the needle within the needle actuator to engage the protrusion of the flexible engagement member with the groove in the shaft section of the needle.

7. The method of claim 6, further comprising, after engaging the protrusion, applying a third longitudinal force in the distal direction on the handle less than the predefined threshold value.

8. The method of claim 7, wherein applying the third longitudinal force includes increasing the third longitudinal force to attain application of the second longitudinal force that transgress the predefined threshold value, and in response to the increasing the third longitudinal force, disengaging the protrusion by causing the engagement member to flex radially outward allowing distal longitudinal movement of the needle.

9. The method of claim 1, wherein the disengaging the flexible engagement member from the groove includes causing the flexible engagement member to flex along longitudinal edges formed by slots in the shaft portion of the needle actuator.

* * * * *